United States Patent [19]

Vogel et al.

[11] 4,323,689
[45] Apr. 6, 1982

[54] 2-HYDROXYPROPYLIMIDAZOLES, THEIR PREPARATION, AND THEIR USE AS OIL-SOLUBLE CORROSION INHIBITORS

[75] Inventors: Hans-Henning Vogel, Frankenthal; Rainer Strickler, Heidelberg; Knut Oppenlaender, Ludwigshafen; Richard Baur, Dannstadt-Schauernheim, all of Fed. Rep. of Germany

[73] Assignee: BASF Aktiengesellschaft, Fed. Rep. of Germany

[21] Appl. No.: 209,959

[22] Filed: Nov. 24, 1980

[30] Foreign Application Priority Data

Dec. 5, 1979 [DE] Fed. Rep. of Germany ....... 2948884

[51] Int. Cl.³ .......................................... C07D 403/00
[52] U.S. Cl. .................................. 548/336; 548/341; 260/348.44; 252/387; 252/390
[58] Field of Search ..................... 548/336, 338, 341

[56] References Cited

U.S. PATENT DOCUMENTS

| 3,280,139 | 10/1966 | Klosa. | |
|---|---|---|---|
| 3,821,241 | 6/1974 | Schmidt et al. | 548/341 |
| 4,088,764 | 5/1978 | Raahe et al. | 548/336 |
| 4,215,220 | 7/1980 | Richter et al. | 548/341 |
| 4,241,060 | 12/1980 | Smithen | 548/336 |

FOREIGN PATENT DOCUMENTS

| 1954706 | 5/1970 | Fed. Rep. of Germany. |
| 2265088 | 4/1976 | Fed. Rep. of Germany. |
| 772830 | 4/1957 | United Kingdom. |

OTHER PUBLICATIONS

J. of Org. Chem. 28 (1963) pp. 2283–2288.

*Primary Examiner*—Ethel G. Love
*Attorney, Agent, or Firm*—Keil & Witherspoon

[57] ABSTRACT

Novel 2-hydroxypropylimidazole derivatives of the formula I

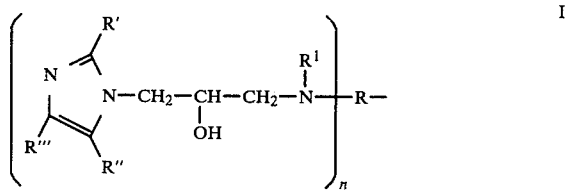

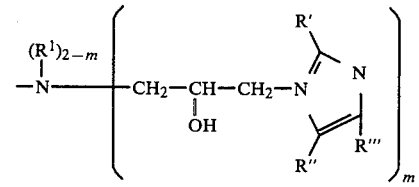

where m is 1 or 2 and n is 0 or 1, $R^1$ is an aliphatic or cycloaliphatic radical of 6 to 21 carbon atoms, R, if n is 0, is an aliphatic, cycloaliphatic, aromatic or araliphatic radical of 6 to 21 carbon atoms and is preferably identical with $R^1$, or R, if n is 1, is a divalent aliphatic or aromatic radical of 2 to 15 carbon atoms or is

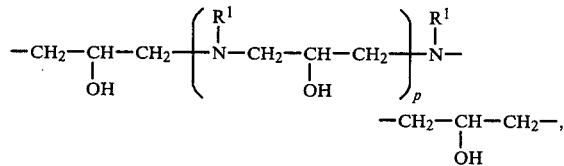

p being 0 or 2, and R', R" and R'" are hydrogen or alkyl of 1 to 4 carbon atoms, and R" or R'" may also be nitro.

2 Claims, No Drawings

2-HYDROXYPROPYLIMIDAZOLES, THEIR PREPARATION, AND THEIR USE AS OIL-SOLUBLE CORROSION INHIBITORS

The present invention relates to novel, substituted 2-hydroxypropylimidazoles, their preparation, and their use as corrosion inhibitors in hydrocarbons.

The hazard of corrosion exists in numerous fields in which metals are in contact with water or with oil-water two-phase systems, for example aqueous emulsions, or with other systems which contain water. It is known that even liquids which contain only small amounts of water, such as gasolines and diesel fuels, can cause corrosion. Condensation water collects in droplets at the bottom of fuel tanks or in pipelines, and, in conjunction with oxygen from the air, has a corrosive action, which can damage the sheet metal and lead layer of tanks, and also the entire fuel feed system of engines. As a rule, corrosion inhibitors are used in an attempt to prevent or counteract the corrosive action of a liquid on machinery and equipment components, vessels, pipe walls and other metallic structural components. To prevent the corrosion of iron, long-chain, high molecular weight organic acids, esters or amines having surfactant properties are normally employed in non-aqueous liquids. German Published Application DAS No. 2,265,008 discloses benzotriazole and tolyltriazole as anti-corrosion additives for protecting non-ferrous metals.

It is true that benzotriazole and tolyltriazole are universally applicable corrosion inhibitors for non-ferrous metals, but because of their complicated synthesis these compounds are expensive, and because of their relatively polar character their solubility in media which essentially only contain aliphatic hydrocarbons is limited. It is therefore the object of the invention to provide oil-soluble corrosion inhibitors which have a very broad spectrum of action and of usefulness, and which do not suffer from the above disadvantages.

We have found, surprisingly, that oil-soluble 2-hydroxypropylimidazole derivatives of the formula I

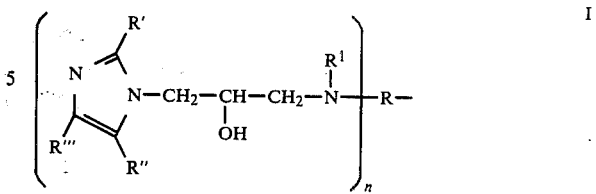

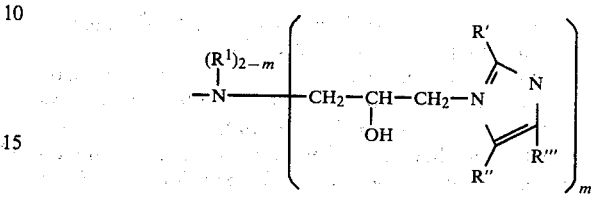

where m is 1 or 2 and n is 0 or 1, $R^1$ is an aliphatic or cycloaliphatic radical of 6 to 21 carbon atoms, R, if n is 0, is an aliphatic, cycloaliphatic, aromatic or araliphatic radical of 6 to 21 carbon atoms and is preferably identical with $R^1$, or R, if n is 1, is a divalent aliphatic or aromatic radical of 2 to 15 carbon atoms or is

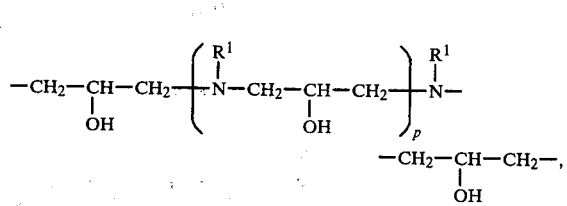

p being 0 or 2, and R', R'' and R''' are hydrogen or alkyl of 1 to 4 carbon atoms, and R'' or R''' may also be nitro, are very good corrosion inhibitors.

These hydroxypropylimidazoles are obtained, for example, by reacting an imidazole, possessing a free N-H group, with a mono- or bis-2,3-epoxypropylamine (III) or a 3-halo-2-hydroxy-propylamine (IV) (with or without addition of an amine of the formula $R^1$—$NH_2$), in the absence of a solvent, or in a conventional solvent such as methanol, ethanol, isopropanol, isobutanol, methylglycol, acetone, methyl ethyl ketone, tetrahydrofuran, dioxane, dimethylformamide, N-methylpyrrolidone, ethyl acetate, toluene, benzene or xylene, at from 0° to 160° C., preferably at from 80° to 120° C.

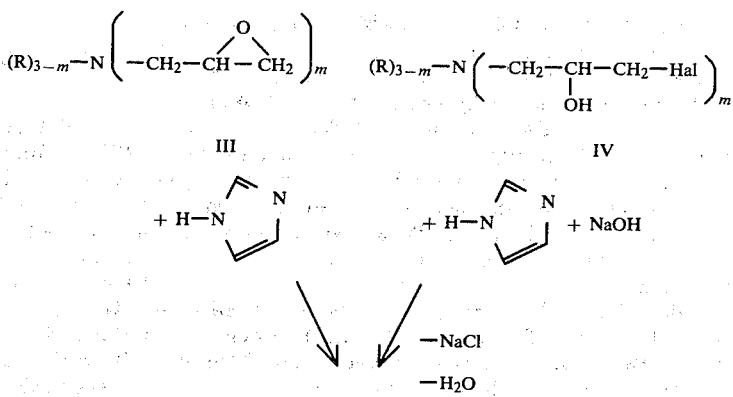

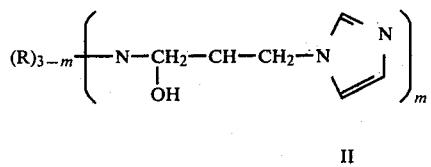

II

The reaction can easily be monitored by titrating the epoxide groups or the free chloride.

3-Halo-2-hydroxypropylamines (IV) are obtainable by reaction of an amine with an epihalohydrin, the methods being described in the literature; the alkaline cyclization of the halohydrin gives, as the next step, the 2,3-epoxypropylamine (III) (U.K. Pat. No. 772,830, J. Org. Chem. 28 (1963), 2,283).

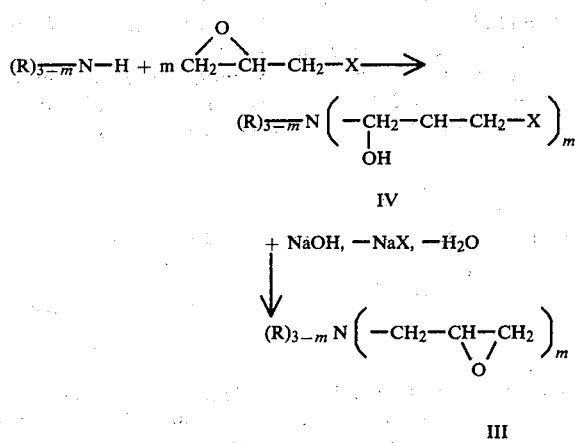

A compound of the formula I, where R is

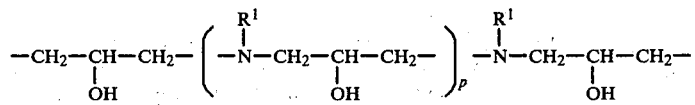

is obtained, for example, if 2-3 moles of the bis-2,3-epoxypropylamine of the formula V

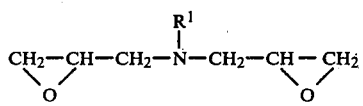

are reacted with 1-2 moles of an amine of the formula $R^1$—$NH_2$ and 2 moles of imidazole.

Examples of amines which may be reacted with an epihalohydrin include alkylamines, eg. n-butylamine, cyclohexylamine, dodecylamine, isotridecylamine and oleylamine, alkoxypropylamines, eg. 2-ethylhexoxypropylamine, arylamines, eg. aniline, which may or may not be substituted by nonionic groups, and polyamines, such as aliphatic or aromatic diamines and polyamines, eg. 4,4'-diaminodiphenylmethane, 4,7-dioxadodecane-1,12-diamine etc.

In the preferred hydroxypropylimidazole derivatives of the formula I, R', R'' and R''' are hydrogen or methyl. Particularly preferred derivatives are those of imidazole itself and of 2-methylimidazole.

A particularly preferred sub-group comprises compounds of the formula II

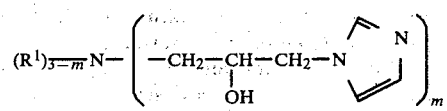

where m has the above meanings and $R^1$ is alkyl or cycloalkyl of 6 to 18 carbon atoms, especially isotridecyl.

The hydroxypropylimidazoles according to the invention are effective as corrosion inhibitors in numerous applications, especially in hydrocarbons.

The applications include industrial heat transfer systems, pumping pipes and other metal equipment for oil-raising equipment, and pipelines, especially fuel pipelines of gasoline engines and diesel engines, as well as all engine components, eg. carburetors, fuel injection pumps, pistons etc., and also fuel storage and transportation tanks. Parts which are particularly prone to corrosion are the components of carburetors (which are made from die-cast zinc=95% of zinc, 4% of aluminum and 1% of copper), as well as the lead-lined parts of fuel tanks.

The corrosion inhibitor can be added to the fuel direct, in concentrations of 0.1-1,000 ppm, preferably of 1-500 ppm. It is also possible to add the inhibitor as part of a commercial fuel additive mixture, consisting of a valve and carburetor cleaner, an oxidation inhibitor, a film-forming anticorrosion additive (to prevent iron corrosion) etc.

The corrosion behavior of water-containing fuels is usually tested on metal coupons in fuel/water mixtures. The action of the product is shown in the Examples which follow.

EXAMPLE 1

N-Cyclohexyl-N,N-bis-(3-imidazolyl-2-hydroxypropyl)-amine (a) 68.1 g of imidazole are fused, under nitrogen, in a 500 ml stirred apparatus equipped with a reflux condenser, dropping funnel, stirrer and contact thermometer. 115.0 g of N-cyclohexyl-N,N-bis-2,3-epoxypropylamine (91.7% pure) are added dropwise in the course of one hour, at 100° C. After a further hour, epoxide is no longer detectable in the reaction mixture. The latter is allowed to cool, and 173.0 g of a pasty product are obtained.

Basic N: 8.2 milliequivalents/g (theory: 8.6 milliequivalents/g)

Total N: 14.2 milliequivalents/g (theory: 14.4 milliequivalents/g)

OH number 317.4: (theory: 322.8)

(b) Corrosion test

A 250 ml glass bottle is filled with 100 ml of super-grade gasoline (Erdölraffinerie Mannheim). The product is added in amounts varying from 10 to 1,000 ppm. 4 ml of distilled water are then added. Test coupons of size 50 mm×20 mm×2 are sanded down (grade 20 abrasive), degreased with toluene, and weighed. The test bottles are shaken vigorously for one minute so as to disperse the water in the gasoline. The metal coupons are introduced and stored for 14 days at 20°–25° C. They are then cleaned with 15% strength hydrochloric acid which contains 1% of propargyl alcohol as a cling inhibitor, degreased and dried. The weight loss is determined by weighing (the results being shown in %o weight loss). As a rule, multiple determinations are carried out.

| Additive | Metal | Lead |
|---|---|---|
| None | | 1.84 %o |
| Compound from Example 1 | 10 ppm | 1.48 %o |
| | 50 ppm | 1.37 %o |
| Additive mixture + | 300 ppm | 0.45 %o |
| | 500 ppm | 0.48 %o |
| Additive mixture plus 1% by weight, based on the mixture, of the compound from Example 1 | 300 ppm | 0.40 %o |
| | 500 ppm | 0.14 %o |

+The additive mixture is a commercial valve and carburetor cleaner, without benzotriazole as corrosion inhibitor.

EXAMPLE 2

N-2-Ethylhexyl-N,N-bis-(3-imidazolyl-2-hydroxypropyl)amine (a) 68.1 g of imidazole (1 mole) are dissolved in 200 ml of ethyl methyl ketone in a 500 ml stirred apparatus equipped with a dropping funnel, reflux condenser, stirrer and contact thermometer. The reaction mixture is then boiled (80° C.) under nitrogen, and 126.3 g of 95.4% pure 2-ethylhexyl-bis-2,3-epoxypropylamine (0.5 mole) are added dropwise in the course of one hour. Finally, the solvent is distilled off; epoxide is no longer detectable in the batch. 194.4 g of pasty N-2-ethylhexyl-N,N-bis-(3-imidazolyl-2-hydroxypropyl)-amine are obtained.

Basic N: 7.7 milliequivalents/g (theory: 8.0 milliequivalents/g)

Total N: 13.2 milliequivalents/g (theory: 13.3 milliequivalents/g)

OH number 293.1: (theory: 297.0)

(b) Corrosion test 2, (carried out similarly to Example 1b)

| Additive | Data in %o weight loss | | |
|---|---|---|---|
| | Metal | Lead | Die-cast zinc 95% of Zn, 4% of Al 1% of Cu |
| None | | 1.53 | 3.72 |
| Additive from Example 2 | 10 ppm | 0.80 | 1.50 |
| | 20 ppm | 0.33 | 1.18 |
| | 30 ppm | 0.34 | 1.07 |
| | 50 ppm | 0.48 | 1.40 |
| Additive mixture without corrosion inhibitor | 300 ppm | 0.45 | 0.05 |
| | 500 ppm | 0.48 | 0.06 |
| Additive mixture | 300 ppm | 0.34 | 0.04 |
| + 1% of the compound from Example 2 | 500 ppm | 0.29 | 0.04 |

EXAMPLE 3

N-Isotridecyl-N,N-bis(3-imidazolyl-2-hydroxypropyl)amine (a) 68.1 g of imidazole (1 mole) are introduced into 250 ml of toluene, at 100° C., in a 1 liter stirred apparatus equipped with a reflux condenser, stirrer, dropping funnel and contact thermometer. 173.9 g of 89.4% pure tridecyl-bis-2,3-epoxypropylamine (0.5 mole) are then added dropwise in the course of one hour, and the mixture is kept at 100° C. for a further hour. Thereafter, the solvent is distilled off under reduced pressure from a waterpump. The residue no longer contains any epoxide groups. 239.6 g of N-isotridecyl-N,N-bis(3-imidazolyl-2-hydroxypropyl)-amine are obtained.

Total N: 11.2 milliequivalents/g (theory: 11.2 milliequivalents/g)

Basic N: 6.2 milliequivalents/g (theory: 6.7 milliequivalents/g)

OH number 243.5: (theory: 250.5)

IR spectrum: bands at 3,500–3,100, 1,520, 1,465, 1,380, 1,235, 1,070 and 750 cm$^{-1}$.

(b) Corrosion test

| Additive | Data in %o weight loss | | | |
|---|---|---|---|---|
| | Metal | Lead | Die-cast zinc | Steel |
| None | | 1.83 | 3.70 | 1.74 |
| Compound according to Example 3a | 10 ppm | 0.40 | 1.22 | |
| | 50 ppm | 0.55 | 1.20 | |
| | 100 ppm | 0.45 | 1.01 | |
| | 500 ppm | | | 0.09 |
| | 1,000 ppm | | | 0.08 |
| Additive mixture without corrosion inhibitor | 100 ppm | 1.91 | | |
| | 300 ppm | 0.68 | 1.55 | |
| | 500 ppm | 0.56 | 1.13 | |
| Additive mixture + 1% by weight of the compound according to Example 3 | 100 ppm | 1.77 | | |
| | 300 ppm | 0.27 | 1.40 | |
| | 500 ppm | 0.36 | 1.28 | |

(c) 185 g of epichlorohydrin (2 moles) and 15 ml of water are introduced, at 30°–35° C., into a stirred apparatus equipped with a reflux condenser, dropping funnel, stirrer and thermometer. At the same temperature, 199 g of isotridecylamine (1 mole) are added dropwise, with slight cooling, and the mixture is stirred until free epichlorohydrin is no longer determinable; this requires 8 hours.

136.2 g of imidazole (2 moles) in 400 ml of isobutanol are then run in, the mixture is brought to 80° C., and at this temperature 280 g of 50% strength potassium hydroxide solution (2.5 moles) are slowly added dropwise. After 4 hours, a chloride determination shows that the chlorohydrin has been completely converted. The mixture is then diluted with about 300 ml of water, the phases are separated and the organic phase is washed again, with a total of 1 liter of water, and is concentrated on a rotary evaporator. 305 g of a viscous product remain; the IR spectrum of the product is identical with that of the product from Example 3a.

(d) Corrosion test

| Additive | Metal | Lead | Die-cast zinc |
|---|---|---|---|
| None | | 1.83 | 3.70 |
| Compound according to Example 3b | 10 ppm | 0.60 | 1.61 |
| | 50 ppm | 0.52 | 1.78 |
| Additive mixture without added corrosion inhibitor | 300 ppm | 0.68 | 1.55 |
| | 500 ppm | 0.56 | 1.13 |
| Additive mixture + 1% by weight of the compound according to Example 3b | 300 ppm | 0.23 | 1.38 |
| | 500 ppm | 0.24 | 0.99 |

EXAMPLE 4

Di-2-ethylhexyl-(3-imidazolyl-2-hydroxypropyl)-amine (a) 241.5 g of di-2-ethylhexylamine (1 mole) are run into 92.5 g of epichlorohydrin (1 mole) and 10 ml of water at 35° C., in a 1 liter stirred flask equipped with a dropping funnel, stirrer, thermometer and reflux condenser, and the mixture is then kept at this temperature for 22 hours. At that point, there is no longer any free epichlorohydrin in the reaction mixture. 68.1 g of imidazole (1 mole) in 400 ml of isobutanol are then run in, the mixture is heated to 100° C., and 140 g of 50% strength potassium hydroxide solution (1.25 moles) are added dropwise in the course of two hours.

After 3 hours, 1.13 milliequivalents of chloride/g are detectable in the batch. The batch is cooled and is repeatedly washed with water, using a total of 1.5 liters of the latter. After concentrating the organic phase under reduced pressure, 273 g of di-2-ethylhexyl-(3-imidazolyl-2-hydroxypropyl)-amine remain.

Total N: 7.9 milliequivalents/g (theory: 8.2 milliequivalents/g)
Basic N: 5.0 milliequivalents/g (theory: 5.5 milliequivalents/g)
OH number 158.9: (theory: 153.4)

| Additive | Metal | Lead | Die-cast zinc |
|---|---|---|---|
| None | | 1.84 | 3.49 |
| Compound according to Example 4 | 50 ppm | 1.30 | 2.28 |
| Additive mixture without corrosion inhibitor | 500 ppm | 0.48 | 0.06 |
| Additive mixture + 1% of the compound according to Example 4 | 500 ppm | 0.29 | 0.04 |

EXAMPLE 5

Oligo-N-tridecyl-imidazolyl-hydroxypropylamine (a)

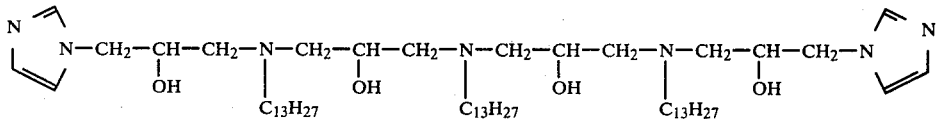

68.1 g of imidazole (1 mole) are introduced into 250 ml of isobutanol at 100° C., in a 1 liter stirred apparatus equipped with a reflux condenser, stirrer, dropping funnel and contact thermometer. 347.8 g of 89.4% pure tridecyl-bis-2,3-epoxypropylamine (1 mole) are added dropwise in the course of one hour, followed by 99.5 g of isotridecylamine (0.5 mole), and the mixture is kept at 100° C. for a further hour. The solvent is then distilled off under reduced pressure from a waterpump. The residue no longer contains any epoxide groups. 509 g of an oligo-tridecyl-imidazolylhydroxypropylamine are obtained.

Total N: 6.9 milliequivalents/g (theory: 7.3 milliequivalents/g)
Basic N: 4.9 milliequivalents/g (theory: 5.2 milliequivalents/g)

(b) Corrosion test: Compound according to Example 5a

| Additive | Metal | Lead | Die-cast zinc |
|---|---|---|---|
| 0 ppm | | 0.82 ‰ | 3.57 ‰ |
| 10 ppm | | 0.12 ‰ | 2.62 ‰ |
| 20 ppm | | 0.12 ‰ | 0.46 ‰ |
| 50 ppm | | 0.20 ‰ | 0.37 ‰ |

EXAMPLES 6 TO 12

The following compounds were prepared, and tested, as described in Example 2:

TABLE

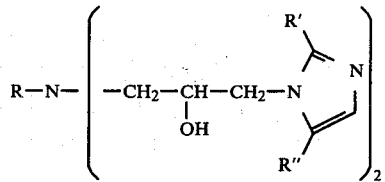

| Compound Amount: 50 ppm in each case | Total N (Theory) in milli-equivalents/g | OH-number (theory) | Relative erosion in ‰ | | |
|---|---|---|---|---|---|
| | | | Lead | Die-cast zinc | Copper |
| Blank | | | 0.82 | 3.51 | 0.04 |
| Example 6 R = n-$C_{12}H_{25}$ R' = R" = H | 11.3 (11.5) | 262.5 (258.6) | 0.33 | 0.83 | |
| Example 7 R = Oleyl R' = R" = H | 10.2 (9.7) | 228.5 (217.5) | 0.30 | 0.62 | |
| Example 8 R = $C_3H_6OC_{13}H_{27}$ R' = R" = H | 9.1 (9.9) | 218.8 (221.8) | 0.04 | 0.084 | |
| Example 9 R = $C_3H_6OC_8H_{17}$ R' = R" = H | 10.6 (11.5) | 239.3 (257.5) | 0.22 | 0.76 | |
| Example 10 R = $C_{13}H_{27}$ R' = $CH_3$, R" = H | 10.2 (10.5) | 227.5 (235.8) | 0.30 | 0.49 | 0.01 |
| Example 11 R = $C_{13}H_{27}$ R' = $C_3H_7$, R" = H | 8.8 (9.4) | 218.0 (210.9) | 0.25 | 0.41 | 0 |
| Example 12 | 11.9 | 216.5 | | | |

TABLE-continued

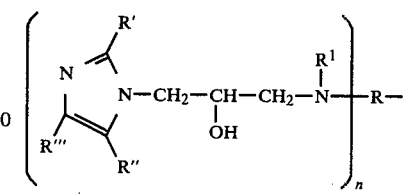

| Compound<br>Amount:<br>50 ppm in<br>each case | Total N<br>(Theory)<br>in milli-<br>equivalents/g | OH-number Relative erosion in °/₀₀ | | |
|---|---|---|---|---|
| | | (the-<br>ory) | Lead | Die-<br>cast<br>zinc | Cop-<br>per |
| R = C₁₃H₂₇<br>R' = H, R" = NO₂ | (13.0) | (208.6) | 0.12 | 0.40 | 0.01 |

Corrosion test on copper in the presence of 2-hydroxypropylimidazoles

Test method:

Copper strips (100×8×2 mm) are tested in cylindrical glass test vessels (as in DIN 51,538, height 180 mm, diameter 40 mm). The strips are rubbed down wth 150-grade emery cloth, degreased with toluene and weighed. Test solution: solvent raffinate, viscosity 6 mm²/s at 100° C., containing 50 ppm (by weight) of dissolved sulfur and the inhibitor to be investigated.

The samples are left to stand for 3 or 6 hours in a drying oven and are assessed visually after they have cooled to room temperature.

Rating scale:

Rating 1—unchanged, no attack
Rating 2—reddish tarnish
Rating 3—up to 50% of the metal surface is black
Rating 4—up to 80% of the metal surface is black
Rating 5—more than 80% of the metal surface is black

TABLE

Corrosion of copper in lubricating oil according to ASTMD 130, in the presence of sulfur

| Product | Rating after 3 hours at an additive content (ppm) of | | Rating after 6 hours at an additive content (ppm) of | |
|---|---|---|---|---|
| | 100 | 500 | 100 | 500 |
| Blank | | 4-5 | | 5 |
| Example 3 | 2 | 1 | 1 | 1 |
| Example 4 | 2 | 1 | 2 | 1 |
| Example 5 | 1 | 1 | 1 | 1 |
| Example 10 | 1 | 1 | 1 | 1 |
| Example 11 | 1 | 1 | 1 | 1 |
| Example 12 | 1 | 1 | 2 | 1 |

TABLE-continued

Corrosion of copper in lubricating oil according to ASTMD 130, in the presence of sulfur

| Product | Rating after 3 hours at an additive content (ppm) of | | Rating after 6 hours at an additive content (ppm) of | |
|---|---|---|---|---|
| | 100 | 500 | 100 | 500 |
| Benzotriazole | 2 | | 2 | |

We claim:

1. A 2-hydroxypropylimidazole derivative of the formula I

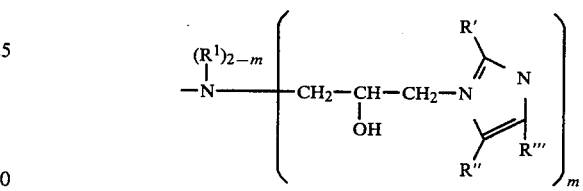

where m is 1 or 2 and n is 0 or 1, with the proviso that m+n is 2, $R^1$ is an aliphatic or where m is 1 or 2 and n is 0 or 1, $R^1$ is an aliphatic or cycloaliphatic radical of 6 to 21 carbon atoms, R, if n is 0, is an aliphatic, cycloaliphatic, aromatic or araliphatic radical of 6 to 21 carbon atoms and is preferably identical with $R^1$, or R, if n is 1, is a divalent aliphatic or aromatic radical of 2 to 15 carbon atoms or is

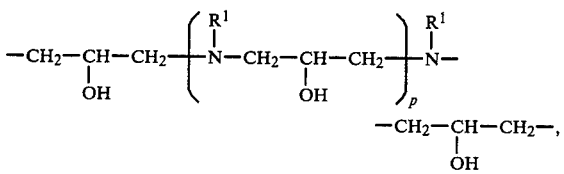

p is 0 or 2, and R', R" and R"' are hydrogen or alkyl of 1 to 4 carbon atoms, and R" or R"' may also be nitro.

2. A 2-hydroxypropylimidazole derivative of the formula

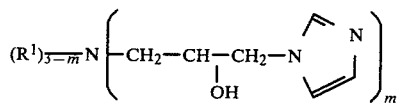

where $R^1$ is alkyl or cycloalkyl of 6 to 18 carbon atoms and m is 2.

* * * * *